(12) United States Patent
Mohr et al.

(10) Patent No.: US 6,643,599 B1
(45) Date of Patent: Nov. 4, 2003

(54) AUTOMATED MACHINE AND METHOD FOR FRUIT TESTING

(76) Inventors: Charles L. Mohr, 1440 Agnes St., Richland, WA (US) 99352; Brandt C. Mohr, 1440 Agnes St., Richland, WA (US) 99352

( * ) Notice: Subject to any disclaimer, the term of this patent is extended or adjusted under 35 U.S.C. 154(b) by 63 days.

(21) Appl. No.: 09/690,147

(22) Filed: Oct. 17, 2000

(51) Int. Cl.$^7$ ................................................ G01N 3/40
(52) U.S. Cl. .................... 702/108; 702/138; 702/41; 73/81; 73/78
(58) Field of Search .................... 702/41, 108, 116, 702/42, 43, 138, 127; 73/79, 81, 427, 82, 85; 30/113.1, 113.2, 113.3; 99/489–493

(56) References Cited

U.S. PATENT DOCUMENTS

| | | | |
|---|---|---|---|
| 3,406,566 A | 10/1968 | Livingston et al. ............. 73/81 |
| 3,470,737 A | 10/1969 | Fridley ........................... 73/81 |
| 3,732,727 A | 5/1973 | Hinnergardt et al. ........... 73/81 |
| 4,061,020 A | 12/1977 | Fridley et al. .................. 73/81 |
| 4,107,985 A | * 8/1978 | Sommer ................. 73/862.633 |
| 4,331,026 A | 5/1982 | Howard et al. ................. 73/81 |
| 4,479,424 A | * 10/1984 | Carroll .......................... 99/502 |
| 4,621,523 A | 11/1986 | Shabel et al. ................... 73/81 |
| 4,657,097 A | * 4/1987 | Griffen ........................ 177/211 |
| 4,884,696 A | * 12/1989 | Peleg .......................... 209/545 |
| 4,937,924 A | * 7/1990 | Leuchtenmuller ............ 28/107 |
| 5,315,879 A | 5/1994 | Crochon et al. .............. 73/818 |
| 5,365,457 A | 11/1994 | Madigosky ................. 364/506 |
| 5,372,030 A | 12/1994 | Prussia et al. ................. 73/37 |
| 5,433,215 A | 7/1995 | Athanasion et al. ........ 128/774 |
| 5,591,902 A | * 1/1997 | Castagner ...................... 73/84 |
| 5,616,857 A | 4/1997 | Merck, Jr. et al. ............... 73/82 |
| 5,691,473 A | * 11/1997 | Peleg ........................... 73/573 |
| 5,760,312 A | * 6/1998 | MacKay et al. ............... 73/818 |
| 5,850,044 A | * 12/1998 | Spletzer ................. 73/862.041 |
| 5,918,266 A | * 6/1999 | Robinson ..................... 73/37.5 |
| 6,142,010 A | * 11/2000 | Merck, Jr. et al. ............... 73/81 |
| 6,240,766 B1 | * 6/2001 | Cawley ...................... 73/12.01 |
| 6,247,356 B1 | * 6/2001 | Merck, Jr. et al. ............... 73/82 |
| 6,332,364 B1 | * 12/2001 | Buschmann et al. .......... 73/788 |

FOREIGN PATENT DOCUMENTS

EP  0439405 A1  * 7/1991  ............ G01N/3/42

OTHER PUBLICATIONS

"HortPlus Quick Measure Penetrometer System", User Manual and Fact Sheet. Jan., 2000.*

* cited by examiner

Primary Examiner—Marc S. Hoff
Assistant Examiner—Jeffrey R West
(74) Attorney, Agent, or Firm—Keith S. Bergman (57) ABSTRACT

A fruit tester provides a motor driven intrusive plunger with associated sensors to determine digital data indicative of plunger position, force resisting plunger intrusion and constant pressure creep. Sensor data is presented to a computer for storage, analysis and feedback control of the plunger. The plunger powering train includes a belt driven ball screw translator to convert rotary to linear motion and an "S" type stress block with plural bridge interconnected strain gauges to sense pressure resisting intrusion to allow accurate measurements. Methods of analysis are disclosed to determine both resistance to plunger penetration and plunger creep at fixed pressure, in each of at least two concentric zones of a fruit, which are related by software for accurate determination of fruit condition as a function of time, both present and future.

10 Claims, 5 Drawing Sheets

AUTOMATED MACHINE AND METHOD FOR FRUIT TESTING

II. BACKGROUND OF INVENTION

IIA. RELATED APPLICATIONS

There are no applications related hereto heretofore filed in this or any foreign country.

1. Field of Invention

Our invention relates generally to measuring and testing, and more particularly to a mechanized penetration type tester that is computer operated and serviced for such testing and processes for fruit testing allowed by the tester.

2. Background and Description of Prior Art

The determination of the ripeness and the maturational state of fruit has been a human desire probably as long as fruit has been used as a food product. Through the history of such determinations the process has devolved from subjective tastable, visual and manual inspection to mechanized and sophisticated somewhat objective procedures, but substantial problems still remain to be resolved to provide meaningful objectivity. The instant invention seeks to solve or alleviate various of these remaining problems, especially as they relate to softer fruits of the pippin and drupe types.

Visual inspection and manual manipulation were early found to be only rudimentary indicators of ripeness and not indicative to any substantial degree, if at all, of maturational state, both by reason of their substantial subjectivity and their lack of any substantial functional relationship to the characteristic sought to be determined. Both methods are still widely used, however, not only by unsophisticated consumers, but also by professionals.

In the early development of more objective fruit testing, the firmness of fruit, or more properly its resistance to pressure deformation or plunger penetration, were found to be more reliable indicators of ripeness and maturation state than visual appearance, manual manipulation and other similar subjective determiners. In modern fruit testing measures of firmness are more widely used as indicators of the fruit condition than are more subjective attributes. As the desire for increased accuracy of fruit testing grew, the testing processes passed from the partially subjective manually manipulable penetration processes to the greater objectivity of mechanically controlled testing devices, firstly of the manually operated type the and subsequently of the mechanically powered and controlled type, to increase accuracy, reliability and repeatability of the testing results. Mechanical testers have developed along the lines of both destructive or penetration type devices and nondestructive or impingement type devices, with representatives of each type of device being used in the modern day fruit testing arts.

Probably the most commonly used present day fruit tester, and that which often serves as the determiner of fruit quality for regulatory agencies, is a manually operated intrusion type tester that provides a cylindrical plunger which is inserted by direct manually applied force into the meat of a fruit to an often variable distance by an operator with measurement only of the maximum force required for insertion being determined and used as the indicator of fruit quality. Such testers provide quite variant results when determined by repeatability, are fairly unreliable in determining fruit ripeness and are substantially unreliable in determining the state of fruit maturation, which is indicative of the course of future development and especially of shelf life of the fruit. The modern trend in private, as opposed to regulatory, testing devices has been toward more sophisticated non-destructive impingement type devices that measure force required for impingement of an object into a fruit surface without skin rupture or the amount of impingement caused by a predetermined force applied on the surface of the fruit by an object or a pressurized gas stream.

The instant mechanism differs from this current and other known fruit testing apparatus by providing a computer controlled intrusive plunger that is mechanically forced into a fruit to a substantial predetermined depth at constant velocity, constant load or a combination of both for measurement in rapid sequence of the mechanical resistance to plunger penetration throughout the length of the plunger's intrusive course. The mechanism provides an electrically powered motor that drives a ball-screw motion translator through a transmission mechanism. The motor has an attached encoder and associated control circuit that regulate the velocity and rotational direction of the motor and thereby the linear velocity and displacement of the plunger responsive to software generated computer commands. The plunger is supported through a load cell which measures the force applied to the plunger throughout its trajectories. The plunger displacement, velocity and applied force measurements are communicated to the associated computer by feedback circuits for recordation and analysis at approximately 30,000 sequential sampling points along a single plunger trajectory.

Prior testers that have provided intrusive plunger type testing of fruit or similar penetrable products generally have not provided for the accurate determination of force resisting plunger penetration at closely spaced and positionally determinable points along a predetermined plunger trajectory and are distinguished from the instant mechanism in this regard. Additionally prior devices are not known to have allowed the selective determination of resistive force of a fruit to plunger penetration at either constant velocity or constant load, to have provided sufficient accuracy in control and measure of plunger speed and position to provide consistently repeatable results and have not determined penetration resistance at such small increments as is allowed by the instant device.

The accuracy of control and measurement of the instant tester arises from the computer controlled and electronically sensed mechanical structure that provides a motor powering a speed reducing cog belt transmission that operates a ball screw motion translator to lineally move a plunger interconnected through an intervening strain gauge block having four strain gauges interconnected in an amplified bridge circuit for force measurement. This type of finely controllable and accurately determinable drive structure is not known to have been previously used for penetration type fruit testing purposes.

The development of such a precision tester has given new insight not only into existing fruit condition, but also into the state and theory of the fruit maturation process itself which has allowed development of new methods for determining ripeness, life stage, condition and future development as a function of time. The tester thusly provides both a scientific informational tool and a practical economic tool to aid determination of conduct for dealing with fruit, both before and after picking. It has been found by accurate and fine measurement at closely placed intervals along a fruit radius that resistance to plunger penetration varies considerably in different parts of a fruit and that this variance is more functionally related to the physiological state of the fruit, and especially to maturation, than is an average or maximum measure of resistivity to plunger penetration. This functional relationship and various of its patternations and their relationships to each other have been used to develop new and different measures of fruit maturation and to give new insight into the nature of that process to allow it to be more meaningfully and accurately used in dealing with fruit throughout the various developmental stages of its life span.

The peripheral zone of most fruits, and especially of apples, generally provides less resistance to plunger penetration than the radially medial or central core area in any state of fruit maturation, prescinding from the initial force required to penetrate the fruit skin.

With the finer analysis allowed by the instant tester it has been found that the physical characteristics commonly associated with fruit ripeness and quality vary considerably in different radial zones of the fruit at any given time, with characteristics commonly associated with ripeness and with subsequent deterioration occurring at different rates in different radial zones of the fruit, so measurement of firmness in the outer layer is a poor predictor of internal fruit condition. This finding has allowed measurements of characteristics in different radial zones of a fruit to both accurately determine the existing state of the fruit and also serve as an accurate means of predicting the change in the nature of the fruit at future times. This has allowed development of methods and processes for use with the tester that provide accurate prediction of ripeness, which heretofore often has been related to the balance of starch and sugar content, and of subsequent consumer desirability, which largely has been related to crispness or firmness of the fruit meat especially in the outer peripheral zone. The tester also allows accurate predictability of acceptable limits for these conditions and determination of the time when the limits will be attained to make the fruit unacceptable.

Processes have been developed and are presented for establishing numerical determination and determination of limits for fruit quality from combined measures of parameters derived from data developed through an entire fruit radius, especially to determine the desirability or quality of the fruit at the time of measurement. Comparative processes have also been developed and are presented to use the data within different radial zones of a fruit to not only provide accurate numerical indicators of quality, but also to relate the parameters in the different zones to each other to provide accurate indicators of the state of fruit maturation and a reliable method of predicting the future state of maturation of the fruit at future times. The measurement of parameters may be continuous through the entire fruit radius or more simply may be based on measures in three logically distinguishable zones of a fruit comprising and outer peripheral zone adjacent the fruit skin, a medial meat zone and the central core zone, or may be otherwise differentiated and refined to provide more detailed and accurate measures for particular types of fruit and particular conditions to be determined. These processes are distinguished essentially from maximal, minimal or gross averaging processes for determining fruit characteristics without regard to the area where the determined parameters are present. The analyses presented by our processes generally have not been possible with prior testing apparatus which did not provide sufficient reliability to allow repeatability of the tests to any substantial degree and have not heretofore been used in commercial or regulatory testing.

Our invention resides not in any one of these features individually, but rather in the synergistic combination of all of the structures of our tester which necessarily give rise to the functions flowing therefrom and the analysis processes essentially related thereto, as herein specified and claimed.

III. SUMMARY OF INVENTION

Our tester provides a plunger intrusion-type mechanism and an associated computer for control of the mechanism and for recordation, presentation and analysis of data sensed by the mechanism. An electrically powered variable speed motor carries an optical encoder to sense rotary direction and speed data, which is transmitted through feedback circuitry to the associated computer for analysis to determine control data to maintain preprogrammed motor function. Rotary motion is transmitted from the motor through a speed reducing cog-belt transmission to a ball screw motion translator that interconnects a strain block which in turn carries an intrusion plunger for linear motion. The strain block carries plural strain gauges interconnected by a bridge circuit to sense resistance to plunger penetration into a fruit and transmit that data to the associated computer. Preprogrammed computer software determines plunger position and resultant penetration into a fruit at either predetermined plunger speed or constant plunger resistive pressure in fine increments at least as small as one in 32,000 parts over the plunger trajectory and stores this data in computer memory.

Processes allowed by the fine measurement of parameters are set forth to determine and numerically represent the maturation state and present condition of fruit, generally of either pippin or drupe types, by analyzing the data through a radius of the fruit or in radial zones. Processes are also set forth for numerically determining and predicting the future maturation state of the fruit at future times by comparing the functional relationships of parameters within different radial zones.

In providing such a mechanism and associated processes it is:

A primary object to provide a plunger type intrusive tester that is serviced by a computer to allow measurement of plunger position at least 30,000 data points in a radial trajectory into a fruit and resistance to plunger penetration with a accuracy of at least 0.001 pound over a radial trajectory extending from the periphery to the center of the core area of a pippin or to the stone of a drupe.

Another primary object is to provide such an intrusive tester that has a mechanism controlled by computer output data determined from mechanism input data with all data transferred between the mechanism and computer through feedback type circuitry.

A further object is to provide such a tester that is of relatively small and portable nature and may be battery powered for field testing.

A further object is to provide mechanism for such a tester comprising a variable speed motor driving a cog-belt type speed reducing transmission that drives a ball-screw motion translator to move a plunger coupled through a strain gauge in a linear course to accurately measure plunger position, velocity and force resisting plunger motion, when coupled through electronic sensors and controllers with a controlling computer.

A further object is to provide such a tester that measures resistance to plunger penetration both at constant plunger velocity and at constant force resisting plunger penetration.

A still further object is to provide such apparatus and processes for measurement and determination of fruit condition that may simulate the results of present day manual impingement testing, but with substantially greater accuracy and repeatability.

A still further object is to provide such apparatus and processes that measure resistance to plunger penetration in predetermined radial zones of a fruit to allow comparison of the parameters in different zones to provide an accurate indicator of the present state and maturity of the fruit, methods for estimating fruit condition at future times, methods to estimate the time of ripeness of immature fruit for picking and the commercially acceptable life span of mature fruit.

A still further object is to provide such a tester that is of new and novel design, of rugged and durable nature, of simple and economic manufacture and one that provides accurate and repeatable test results with various fruits, vegetables or similar materials that are tested by plunger penetration and to provide essentially related processes for the determination of present condition, maturation state, future development and consumer desirability as allowed by reason of the fine, accurate and detailed data provided by the tester.

Other and further objects of our invention will appear from the following specification and accompanying drawings which form a part hereof. In carrying out the objects of the invention, however, it is to be remembered that its accidental features are susceptible of change in design, configuration and accidental features with only preferred and practical embodiments of the best known modes being illustrated and specified as required.

IV. BRIEF DESCRIPTION OF DRAWINGS

In the accompanying drawings which form a part hereof and wherein like numbers of reference refer to similar parts throughout.

V. DESCRIPTION OF PREFERRED EMBODIMENT

Our tester generally comprises frame 9 enclosing testing chamber 10 in its lower portion and carrying powering train 11 to move plunger structure 12 within the testing chamber to operatively engage fruit 76 positioned within the testing chamber. Control member 13 carried by the frame 9 receives software generated control data from associated computer 14 to operate the powering train and senses, receives and transmits process data to the computer for analysis, displays and recordation.

Frame 9 provides rectilinear base 15 supporting elongate upwardly extending left side 16 and peripherally similar right side 17 in parallel lateral alignment on the elongately medial portion of the base. Top 18 is structurally carried between the upper portions of the right and left sides 16 and 17. Back plate 19 is carried on the rearward facing edges of the sides 16, 17 in their medially upper portions. Forward circuitry support panel 20 is carried on the forward edges of sides 16, 17 in their medially upper portions. These frame elements are all structurally joined in their adjacent portions by fasteners 21, in the instance illustrated of a bolt-type, threadedly extending between the joined elements to provide a rigid but disassembleable support frame, portions of which are covered by peripheral cover 22 releasably carried and about the upper portions of the peripheral surfaces of the frame and there positionally maintained by fasteners 21.

The upper surface of base 15 carries centering plate 23 between sides 16, 17. The centering plate 23 is a circular disk with upper surface 24 configured to define a shallow depression formed as an inverted cone having its apex aligned with the axis of the centering plate and defining a central angle between diametrically opposed ruling lines of 160 degrees to support fruit 76 and maintain the fruit in a somewhat centered position by reason of the curvilinear configuration of the fruit, regardless of its orientation. The centering plate 23 is structurally positioned and maintained on the base 15 by threaded fasteners (not shown) extending therebetween, preferably through the base and only partially into the lower portion of the centering plate. The stripper plate 25 is carried between sides 16, 17 spacedly above the centering plate at a distance that allows fruit to be tested to be inserted between the stripper plate 25 and centering plate 23. The stripper plate defines medial hole 26 incrementally larger than a plunger to be used in the tester so that the plunger may extend through hole 26 for unencumbered motion to penetrate a fruit, but yet the stripper plate will prevent motion of the fruit upwardly past the stripper plate when the plunger is extracted from the fruit.

Testing chamber 10 is defined in the lower portion of the frame between base 15, sides 16 and 17 and stripper plate 25 spacedly thereabove. The rearward portion of the testing chamber is enclosed by rear shield 27 having body 27a configured as a semicircular sector of a cylinder with laterally extending coplanar legs 27b extending outwardly from each side edge to fit in adjacency on the lower portions of the rearward facing edges of frame sides 16, 17 where they are positionally maintained by fasteners 28 extending in threaded engagement therebetween. The upper surface of rearward shield 27 structurally carries top cover 29 to prevent entry of downwardly moving debris into the rearward part of the testing chamber 10. Front shield 30 is of a configuration similar to the rearward shield, but preferably has no top cover. One front shield leg 30b carries spaced hinges 31 which are supported by left frame side 16 to allow pivotal motion of the front shield to open for access to the testing chamber 10.

The hinges 31 preferably are of a biased type to provide a null closure mode for the door. A catch (not shown) may be provided to maintain closure if desired. Preferably the front shield body 30a extends spacedly forwardly of the forward portion of peripheral cover 22 so that the forwardly projecting shield portion may be used for manual grasping to aid opening and closing manipulations of the front shield.

Figure 1:
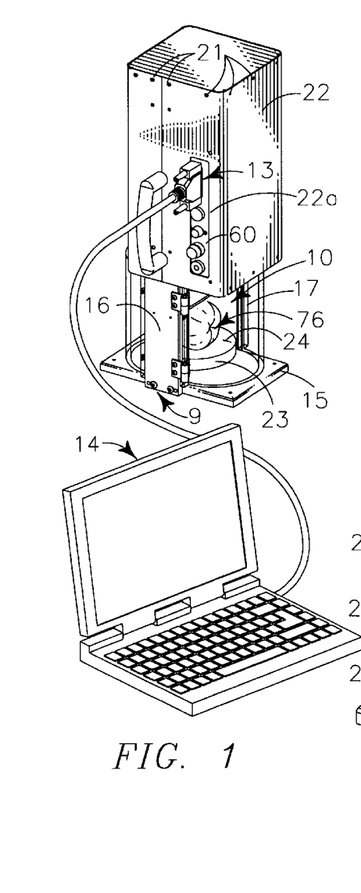
FIG. 1 is an isometric view of our fruit tester interconnected an associated lap-top computer.
Figure 2:
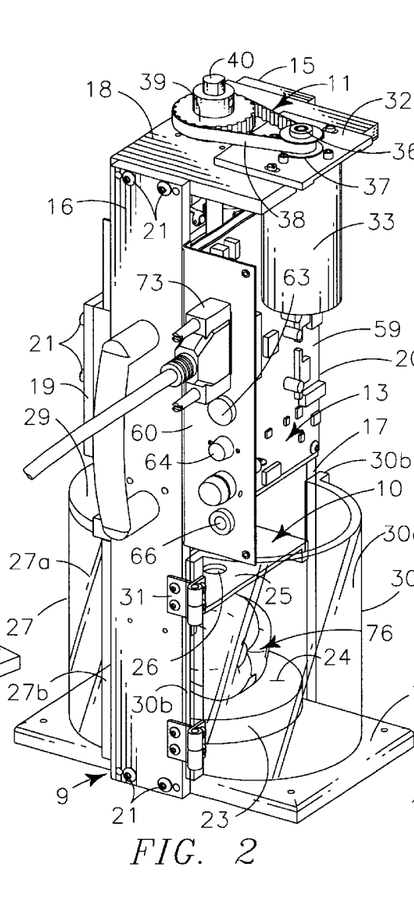
FIG. 2 is an enlarged isometric elevational view of the tester of FIG. 1 with case removed to show various parts, their configuration and relationship.
Figure 3:
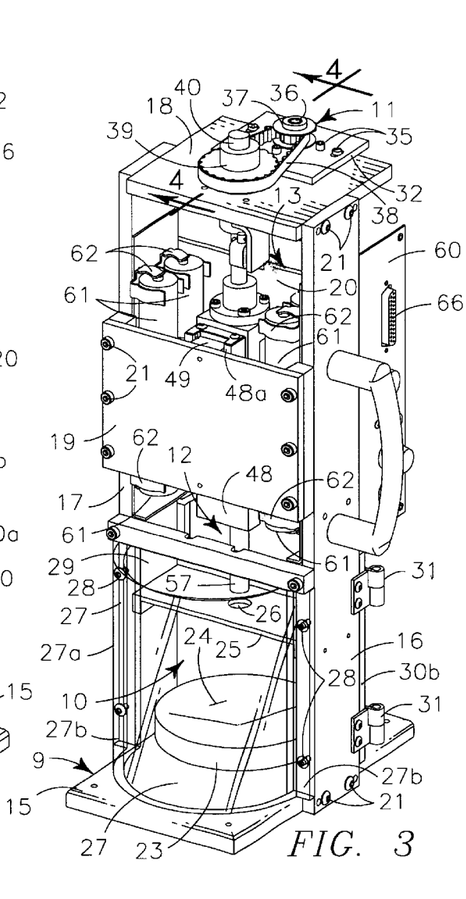
FIG. 3 is an enlarged isometric view of the tester of FIG. 2 rotated ninety degrees in a counterclockwise direction to show various additional components and internal structure.
Figures 4, 10:
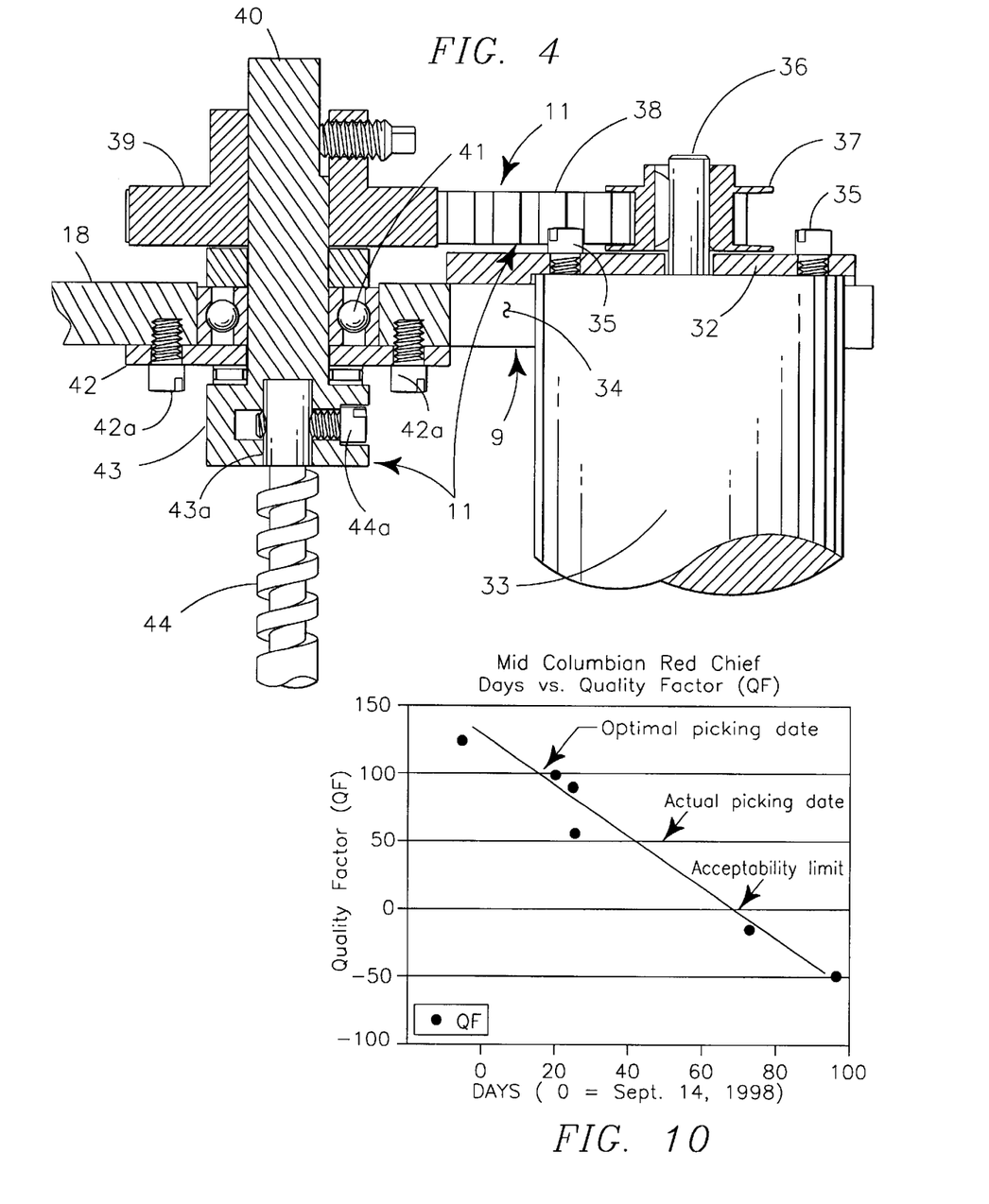
FIG. 4 is an enlarged partial vertical cross-sectional view through the upper portion of the tester of FIG. 3, taken on the line 4—4 thereon in the direction indicated by the arrows, to show details of the powering train and supporting top frame.
FIG. 10 is a graph showing the relationship of the quality factor value to fruit condition for a selected group of Columbian Red Chief apples.

As seen in FIGS. 2, 3 and 4 upper motor support plate 32 is carried on the upper surface of top 18 to mount depending motor 33 in motor orifice 34 defined in top 18 and there positionally maintain the motor by bolts 35 fastenably extending between the motor support plate and the motor casement. Motor drive shaft 36 irrotatably carries cog belt pulley 37 that drives endless cog belt 38 extending rearwardly to operatively communicate about driven belt pulley cog 39 irrotatably carried by screw drive shaft 40. The screw drive shaft 40 is carried in thrust bearing 41 carried in top 18 and positionally maintained against downward motion by bearing plate 42 supported on the undersurface of top 18 by bolts 42a fastenably extending therebetween. The lower end of screw drive shaft 40 defines radially larger collar 43 having medial orifice 43a to receive and irrotatably interconnect the upper end portion of screw shaft 44 by means of bolt 44a extending therebetween.

Figures 5, 7:
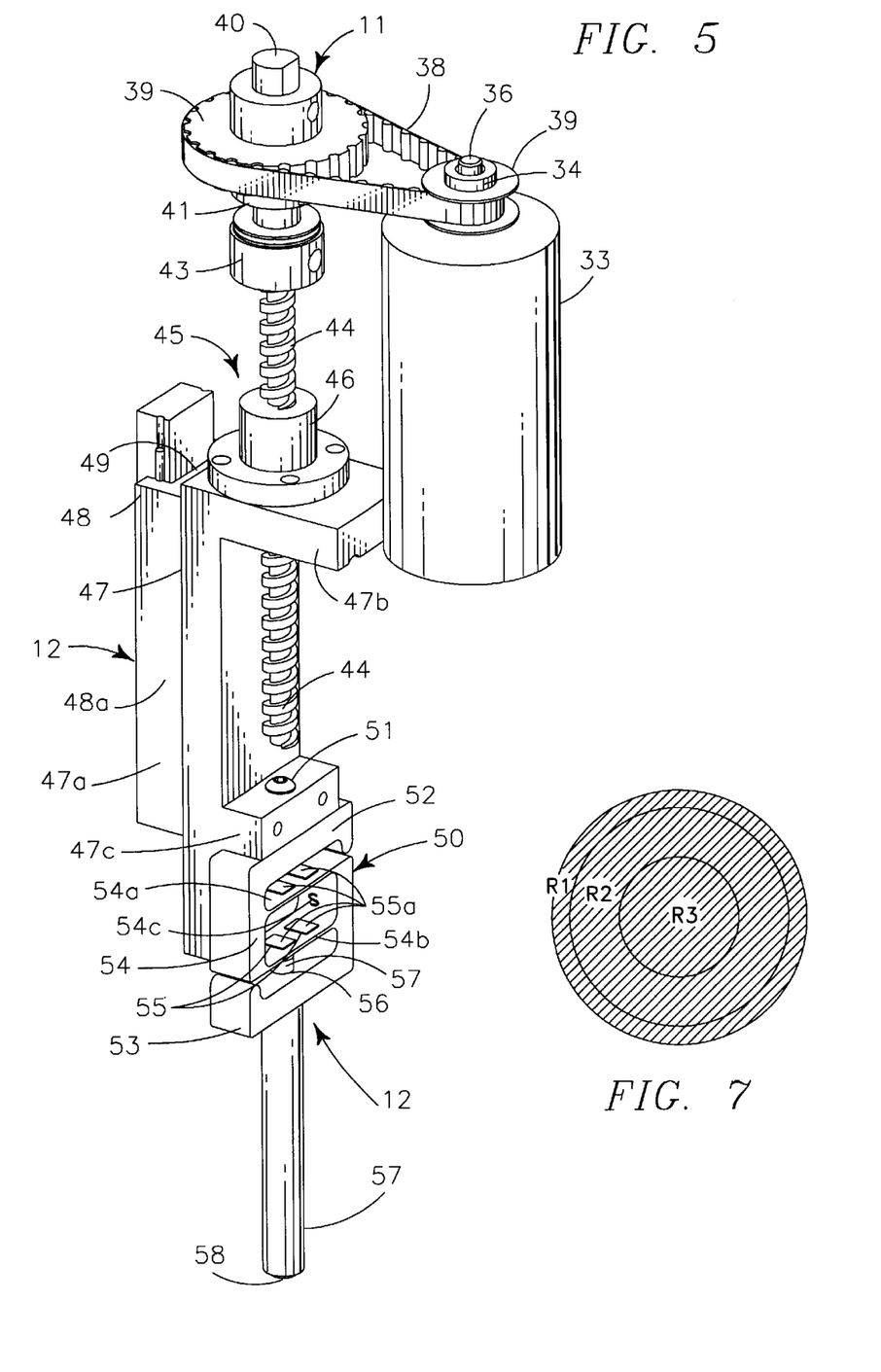
FIG. 5 is an isometric view of the powering train and plunger structure of the tester of FIG. 2 isolated from the tester to better show the various parts and their relationship.
FIG. 7 is an idealized diagram pippin type showing the three logical zones of a pippin type fruit used for data analysis.

As seen in FIG. 5 the screw shaft 44 of ball-screw motion translator 45 depends spacedly below its irrotable interconnection with collar 43 to operatively interconnect translator body 46. The ball-screw translator 45 converts rotary motion of the screw drive shaft 40 into linear motion of the translator body 46 to responsively move plunger structure 12 in a vertical direction. Such ball-screw motion translators have been long known in the mechanical arts and therefore are not described in detail.

The ball-screw translator body 46 is structurally carried by plunger slide 47 depending therefrom. The plunger slide provides vertically elongate rectilinear body 47a having perpendicular forwardly extending horizontal upper leg 47b and lower leg 47c. The translator body 46 is structurally carried on the upper surface of the upper leg and that leg defines an appropriately configured and positioned hole to allow the lower portion of the screw shaft 44 to depend therethrough for vertical motion of the plunger slide 47 on the screw shaft. The distance between the upper leg 47b and lower leg 47c is such as to allow sufficient vertical plunger motion for penetration through at least the upper radius of a fruit to be tested. The slide body 47a carries rearwardly extending, vertically elongate slide rail follower 48 having similar spaced rearwardly extending legs 48a that slidably receive and positionally maintain slide rail 49 therebetween. The slide rail 49 is structurally carried back by 19 of the frame 9 as shown in FIG. 3.

Plunger slide lower leg 47c carries stress block 50, by means of threaded fastener 51 extending therebetween, depending from the lower surface of the lower leg 47c. The stress block is of an "S" type providing similar cantilevered upper leg 52 and lower leg 53 each having laterally opposed vertically extending portions that are interconnected by medial laterally extending body 54 defining a rectilinear orifice 54c to separating cross-sectional smaller upper arm 54a and lower arm 54b of the beam for stress measurement. Laterally medial portions of the upper and lower beam arms 54a, 54b carry spaced strain gauge 55 to measure force imposed between the upper and lower legs 52, 53 of the stress block.

Lower leg 53 of the stress block defines medial threaded hole 56 to receive the threaded upper portion of plunger 57 in vertically adjustable interconnection. The plunger shaft 57 depends from the stress block 50 a spaced distance to allow its penetration to at least the medial portion of fruit 76 to be tested when carried by the centering plate 23. The lower end portion 58 of plunger shaft 57 may be variously configured for particular purposes, but for ordinary testing it is preferred that the plunger end be configured as a segment of a sphere having a radius somewhat greater than the radius of the plunger shaft, though other plunger end shapes are within the ambit and scope of our invention, but may produce somewhat different test results.

Preferably for ease of operation, analysis and accuracy of the entire drive train and plunger assembly are so configured and related that drive shaft 40 and plunger shaft 57 are coaxial on a line that is coincident with the axis of centering plate 23 to allow the plunger to penetrate substantially vertically into a tested fruit to create substantially vertically oriented resistive forces to plunger penetration and eliminate substantially all laterally directed force components. The spherical configuration of plunger end 58 and the fruit's support on the centering plate also combine to eliminate or reduce non-vertical plunger penetration and laterally directed forces caused thereby. The maintenance of vertical radially vertical orientated plunger penetration aids in preventing erroneous, irregular and non-repeatable results in fruit testing.

Control member 13 provides two sided printed circuit board 59 mounted between the vertically medial portions of sides 16, 17 of frame 9, between motor 33 and the adjacent depending portion of powering train 11. The printed circuit board 59 communicates with adjacent perpendicular elongately extending control panel 60 that is externally accessible through orifice 22a defined in peripheral cover 22. The control panel 60 provides a mounting area for electrical connection fixtures and controls that may require frequent access. The circuitry of the control member and of its individual components are not new or novel in and of themselves, but rather their novelty resides only in the particular combination of the various circuitry elements. This circuitry therefore is not set forth in the detail of a circuit diagram, but rather described by reference to the block diagram of FIG. 6. The primary power source for the tester is rechargeable battery 61, which in the instance illustrated comprises four sets of "D" size battery cells carried in similar opposed supports 62, each structurally carried on the interior surfaces of frame sides 16, 17 to provide an operating voltage of approximately 19.2 volts DC. The battery 61 communicates through state meter 63 and power switch 64, both carried on control panel 60, to provide power for the control member. External battery charger 65 may communicate through releasable connector 66 to charge the battery 61 from an external 120 volt AC power source. The battery current passes to power regulator and converter circuitry 67 and thence to voltage regulator 74 to provide +5 volt and −5 volt DC current and +12 volt DC regulating and operating current, all for operation of the various electronic control and sensing elements.

Figure 6:
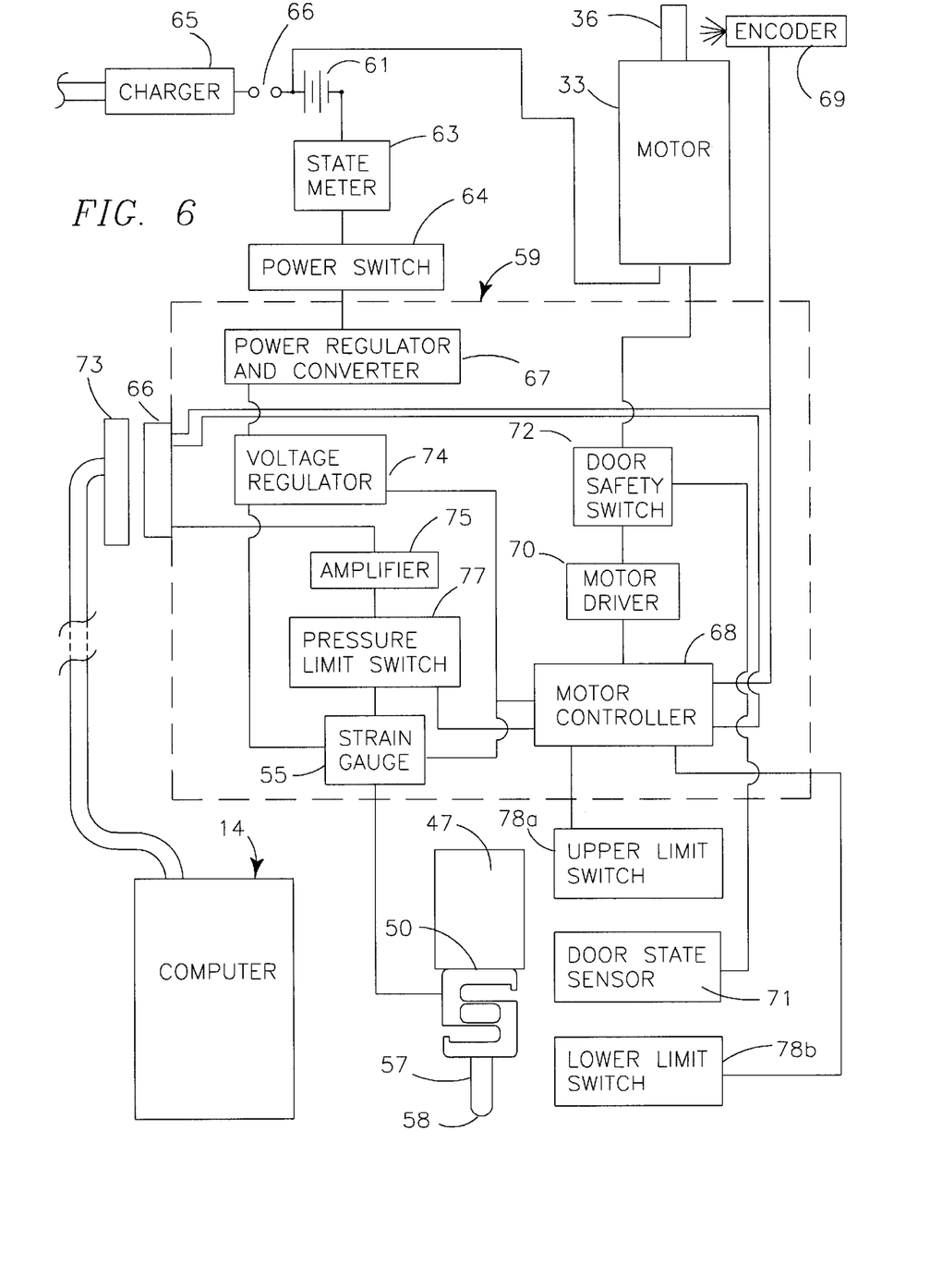
FIG. 6 is a block diagram of the electrical control and data sensing system of the tester.

Motion controller 68 is a special purpose digital processor with embedded software to provide control signals required to cause motor 33 to move through a predefined sequence of motions to move plunger 57 through a predefined testing program herein termed a "trajectory". The trajectory command sequence consists of several data- bites to define motor operating mode, position, speed and acceleration. The movement of motor drive shaft 36 is sensed by optoelectronic shaft encoder 69 mounted on the motor housing adjacent the drive shaft 36. The actual operating parameters of the motor are compared with computer software commanded values to produce error signals for closed loop control. Gain and response signals are responsively communicated from the computer and command interface to the motor controller 68. Motor control signals are responsively sent from the motor controller 68 to motor driver 70 to determine the magnitude of voltage applied to the motor and provide a signed signal to direct the motor rotational direction. These signals are passed through safety switch 72 which interrupts motor operation when the front shield 30 is open as determined by door state sensor 71. The power provided through the motor driver 70 is filtered by capacitors to prevent large peak current draws that may be caused by modulating the battery voltage. The motor driver 70 provides an integrated H-bridge type interconnection of four power switching transistors to allow the full power supply voltage of 19 volts DC to be applied for rotation of the motor drive shaft 36 in either direction. Circuitry is provided to electronically remove, or at least alleviate, transients caused by electronic noise that could interfere with tester data signals. Information is provided by the encoder 69 and combined with strain gauge pressure data to provide indication of excessive pressure. Plunger position limits are determined by upper and lower position sensing microswitches 78a and 78b respectively and plunger motion is limited by pressure limit switch 77.

The parallel port of associated computer 14 is used to pass digital information in both directions between computer 14 and the control member 13. Control instructions are sent from the computer to the control member circuits and measurement data of pressure, plunger position and operational status is returned. The computer parallel port has two addresses for the programs that are used to transfer instruction data to the tester. The first address is a four bit port that is used to send operational commands only. One bit addresses an EPROM to store the other three operational bits. The EPROM converts the operational bits into control signals for the tester members to reset the tester, read contents of a strain gauge analog-digital converter, turn on the excitation voltage for operation of the strain gauge bridge and select the direction of data flow either into or out of the tester.

The second port address is an eight bit data path used to provide input supportative data for the motion control processor commands including the type of command, acceleration rate and position parameters of the plunger. In the output direction this path provides tester data to the associated computer 14 including motion control, processor status, motor position, strain gauge output, motor temperature, plunger limit switches and interrupt requested states.

The strain gauge 55 carried by the stress block 50 provides four sensing elements 55a connected in a full bridge configuration. The bridge is powered through voltage regulator 74 to provide a DC voltage of about 10 volts which may be regulated for scaling adjustment of the strain gauge. If operated continuously, the strain gauge 55 would present a substantial demand on battery power and shorten the period of potential tester operation between charges, so the excitation voltage is switched sequentially to be on only when the strain gauge is being actively read.

The electric output of the strain gauge 55 is small, in the preferred embodiment being about 30 millivolts for 64 pounds of resistive force applied to the tester plunger. This voltage is transformed by amplifier 75 to raise it to 5 volts for accurate digitization. The amplified strain gauge signal is converted to a digital value by an analog-to-digital converter to provide digital resolution of 0.25 ounce per least significant bit and a full scale value of 64 pounds. The strain gauge output is read at selected times determined by a software test program in the controlling computer.

The computer operated software that controls the operation of the tester and records, analyzes and displays the determined data is not novel per se, but only as to its combination with the tester to provide the functions specified. A person of reasonable skill in the software art is capable of providing such software if provided with knowledge of the tester and its operation and specification of the required functional parameters.

The operation of our tester may be understood from the foregoing description of its structures and functions.

A tester formed as specified is attached by a parallel cable communicating from tester parallel connector 66 to parallel port 73 of associated computer 14. The tester is powered by battery 61 through power switch 64 and its operation after institution is controlled by software carried by computer 14. The fruit 76 to be tested, in the instance illustrated an apple, is inserted in testing chamber 10 to rest upon centering plate 23 and the testing chamber front shield 30 is closed to operate switch 72 to allow power to pass to motor 33. The computer software is adjusted to desired parameters for the particular type of test, plunger trajectory and plunger speed and the test is then instituted by the software upon command.

In the preferred embodiment of the tester for apples, encoder 69 distinguishes 1024 data points per motor shaft rotation and corrects motor velocity to within two encoder points for each 256 point sampling interval. The rotary motion of the motor shaft is transmitted from motor 33 through the cog-belt 38 with a 4:1 speed reduction to ball screw translator 45 which has a pitch of 0.125 inch. This mechanical arrangement provides potential sensitivity of 32,768 data points per inch of plunger travel. The force resisting plunger motion is measured by the stress block 50 which has a stiffness of approximately 550 pounds per inch of motion with a measurable sensitivity of at least 0.25 ounce (0.016 pound).

Upon test institution responsive to computer command, the motor first advances the plunger at higher speed to the surface of a fruit to be tested. The fruit surface is detected by the increase in force resisting plunger motion as sensed and indicated by the strain gauge 55. At this point responsive to the sensed force the plunger motion is set to the predetermined velocity for testing the fruit. The diameter of the fruit is computed from the upper surface position with reference to the known centering plate position and the plunger trajectory data and computed center location is sent to the motor controller. The fruit then is tested at each selected interval of plunger displacement and the force resisting plunger penetration is checked for each interval and read as preselected by the software. When the center of the fruit is reached by the plunger, it is withdrawn at a higher speed as selected by the software, the test data may be visually displayed on the associated computer display screen and recorded in the computer memory and the tester is reset for another test.

This testing overcomes deficiencies of the common manually operated test unit that generally is presently employed in the fruit industry by growers, processors, merchandisers and inspectors. The current manual testing method uses an apparatus that measures the maximum resistive force obtained in inserting a plunger, usually of 0.440 inch diameter for apples and 0.31 inch diameter for pears, into a fruit to a depth of approximately 0.3 inch. This manual testing method provides a simple concept but does not provide means for regulating plunger speed as the plunger penetrates into the fruit, and that penetration speed varies widely with different operators and in different portions of the fruit to provide quite variable results. This variability is caused largely by the variance in the viscoelastic properties of the fruit tissue in general and especially in different radial zones of a fruit, as fruit tissue generally will not statically support a plunger under fixed load without displacement. The fruit tissue will creep away from the plunger to relax the resistive load, so the faster the plunger is moved the higher is the load resisting plunger motion and conversely the slower the plunger is moved the lower is the load resisting motion. The differences between this presently standard testing method and that allowed by the instant tester provide substantial information concerning the nature of fruit maturation which in turn has given rise to new and novel testing methods and results which were not heretofore possible with the manually operated intrusive type tester, or in fact with other known impingement testers.

The instant tester in forcing a plunger into a fruit allows plunger penetration at a predetermined constant velocity or at a predetermined constant load and measures the resistance to plunger penetration rapidly and at closely spaced data points throughout the plunger trajectory. In discussing the tester operation herein the term "pressure" is used to indicate the force resisting plunger penetration into a fruit as this term is commonly used in the industry, though the term may not be literally correct as the pressure is functionally related to the configuration of a particular plunger. Most plunger sizes and shapes however, are fairly standardized to make the term reasonably accurate. The instant tester allows measure of resistive pressure with an accuracy of approximately 0.0156 pound and allows data sampling on a time frequency of at least 5000 cycles per second, both with substantial accuracy and repeatability of results. This measurement process has given new detailed insight into the nature of the existing state of a fruit and also of its maturation state and process.

As a fruit matures, and especially an apple, whether on a tree or separated therefrom, the ongoing metabolism causes the internal structure of the fruit to change as a function of time to responsively cause lower pressure resisting the penetration of a tester plunger. This process is not uniform over the entire fruit mass and especially in different radial zones of the fruit. The change in internal structure continues with time, as a fairly direct function of the metabolic process, to eventually result in a fruit that is commercially undesirable. Various historical and handling parameters influence the rate and extent of the metabolic process such as growth history, varietal nature, picking time, storage temperatures and atmosphere, ethylene gas storage processes and especially time of removal therefrom and other similar conditions can have significant effect on the maturation process. The overall influence and results of these various parameters can be well estimated and future developments functionally related thereto with substantial accuracy by the instant tester and testing processes.

Unfortunately current fruit testing practices do not adequately show the fine and subtle changes in fruit to accurately determine its state of maturity during and after the growing season and often historically traditional gross indicators of fruit state such as texture, color, starch and sugar levels are not sufficiently accurate to determine either the present state of the fruit or predict its future development. It has been found with the instant tester and testing processes that in general fruit maturation develops somewhat similarly but sequentially within each of three definable zones of a fruit, though the maturation may vary substantially between those zones at a given time. The zones do not have clearly determinable and definite boundaries and boundaries must generally be determined in individual cases and with particular types and species of fruit, but the relationship of the sequence of maturity in the three zones maintains its essential nature.

As seen in FIG. 7, a fruit defines a first outer radial zone denominated R-1 that extends from the peripheral skin to an arbitrary average depth of approximately 0.320 inch. This depth is determined as the depth normally tested by manual pressure testers of the present day and establishes a basis for determining some relationship between the instant testers and historical testers. A second medial radial zone denominated R-2 comprises the meat region of the fruit where most of the edible portion of the fruit resides. This R-2 zone extends from the R-1 zone inwardly a spaced distance to an innermost R-3 zone. The inner core region of the fruit is designated as the R-3 zone and in general is substantially proportional to the fruit radius. To simplify analysis of data and allow it to be more easily and fully dealt within the instant process, the data has been classified into these three zones, but it must be realized that the only boundaries that have physical definition are the periphery of the fruit or outer surface of the R-1 zone and the core portion or outer surface of the R-3 zone, with the division between the R-1 and R-2 zones having no particular physical determinant but rather being arbitrarily determined.

Manual pressure testing is widely variant in repeatability tests not only because of variations between individual tester manipulators based largely on the velocity of insertion of a plunger to differing depths and determining only a maximum pressure reading, but also because the testing method commonly samples substantially only the R-1 zone of a fruit, and under present standards and practices makes no determination in any substantial portion of the condition of the R-2 or of R-3 zones. Research with the instant tester has suggested that fruit pressure can remain relatively constant in the R-1 zone while internal fruit pressure, and therefore texture and crispness, can continue to decline in zones R-2 and R-3 to provide an erroneous determination not only of the existing state of the tested fruit, but also erroneous indication of its maturation state and consequently inaccurate prediction of its condition at future times. Research has also indicated that the rate of change in fruit pressure in zone R-1 is slower than in the interior zones R-2 and R-3 which change at a more rapid rate to exacerbate the problem.

Figure 9:
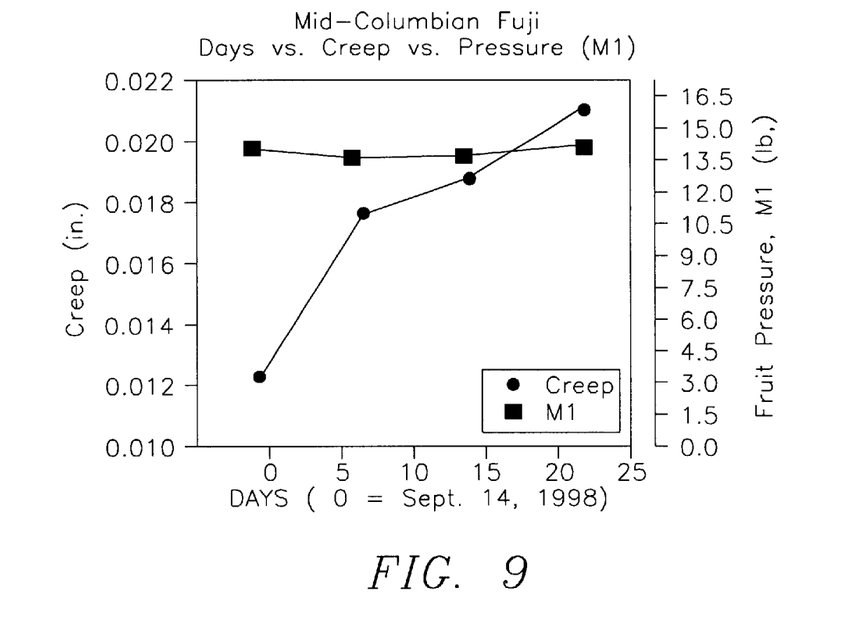
FIG. 9 is a graph showing the difference in creep in a selected group of Columbian Fugi apples of both fresh and overly mature condition as well as fruit pressure in the outer surface region.

The measurement of creep or the displacement occurring at a constant plunger pressure is especially related to apple maturity and adds a new dimension to test data. Certain apple varieties such as the Fuji, are structurally robust enough to be held for long periods on a tree to produce water-core that may be desirable in some but not all marketplaces. Measurements which have been used to determine maturity in the past, such as maximum pressure to plunger penetration in the R-1 zone and starch value, will reach a plateau in such apples and are no longer of value in determining maturation state, as the apple condition remains substantially the same in the R-1 zone while deterioration occurs internally thereof. Creep tests in the R-2 and R-3 zones indicate the internal condition of the apple's maturity which is not determinable by the present testing methods. The relationship of average pressure to creep plotted as a function of time, is illustrated in FIG. 9 for an average group of Washington State mid-Columbia Fuji apples of the 1998 growing season.

Figure 8:
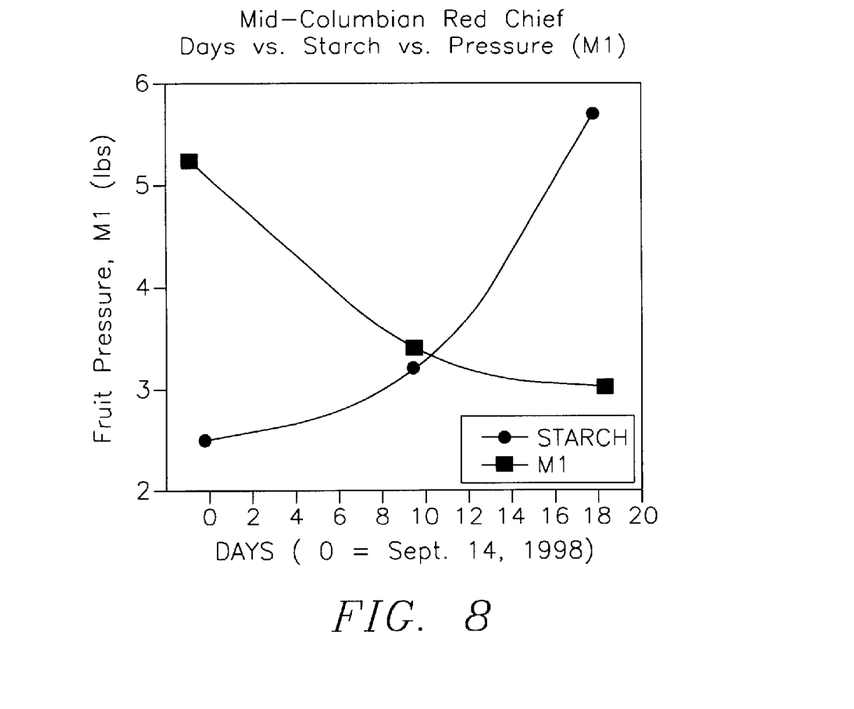
FIG. 8 is a graph showing the relationship of starch values to fruit pressure in a selected group of Columbian Red Chief apples.

The relationship of starch content to internal fruit pressure as a function of time and as determined by the instant tester, is shown in the illustration of FIG. 8 which shows that starch is not a goo d indicator of change in fruit structure as commonly has heretofore been assumed. With time while fruit pressure decreases starch continues to increase to make the fruit less desirable to a consumer. Creep or displacement essentially is a measure of the viscoelastic properties of the fruit meat and in an apple that has just reached maturity there will be substantially no creep in the R-1 zone and little creep interiorly of this zone. In an apple that still retains high pressure readings in the R-1 zone, with further maturity the creep will increase somewhat in that zone and will increase remarkably interiorly in the R-2 zone and especially in the R-3 zone to provide a sensitive indicator of maturation state.

The testing of fruit with the instant apparatus is controlled by software of the associated computer. The software directs a predetermined trajectory for the plunger which for ordinary testing purposes is limited to a total displacement of the upper radius of an individual fruit. That radius is determined by plunger position when the plunger first senses the pressure of initial contact with the upper surface of a fruit carried in the testing chamber on the centering plate by relating this position to the predetermined assumed position of the lower fruit surface resting on the centering plate. The type of data to be determined is preselected as pressure measurement at a constant plunger velocity, pressure measurement at a constant load or a combination of both, with the constant velocity pressure determination being known as a "short test" and the combination determination being known as a "long test". The test then proceeds under control of the computer software for the sensation of data at approximately 30,000 data points along the trajectory with an accuracy of at least 0.015 pound (0.25 ounce) in pressure measure.

In the preferred long test, made with pressure measure and interspersed measurement of creep over specific time intervals, preferably but not necessarily of about two seconds duration, the software moves the plunger at a predetermined velocity as it senses constant velocity fruit pressure over a range, and then stops to measure the trajectory at a predetermined constant pressure over the predetermined time period. This sequence of measurement continues in the software predetermined manner over the entire trajectory. Creep must be measured over a period of time and in general with ordinary apples will vary substantially lineally in the range of 0.1 inch difference in a period of 2.5 seconds under a plunger load of 10 pounds, but may vary on a different functional basis for different fruit species and varieties and for these species and varieties the length of the creep measurement period becomes more important. The data sampling programs are user-determinable by programming of the controlling software, but for general use by unsophisticated users predetermined standardized programs are provided by default by the software.

The data obtained from a test is stored in computer memory for display and analysis. The data presents various possibilities for analysis to determine fruit state, quality and maturation. The elastic modulus of the fruit may be determined. The maximum, minimum and average pressure resisting plunger penetration may be determined for an entire trajectory, in small positionally identifiable zones throughout the trajectory and in each major fruit zone. The creep deformation may be determined in similar zones individually or sequentially with or without constant velocity determination in predetermined or user determinable zones. Various known methods of statistical analysis of resistive pressure and creep for any test mode may be determined for an entire test. Various comparisons of these measurements with predetermined profiles may be correlated to indicate traditionally recognized fruit conditions such as starch pattern, water core, dissolved solids and the like. In general individual samples at each data point are saved in the computer memory and are subsequently available for analysis. All of this data is valuable, especially to sophisticated testers, for determination of fruit state, past history, research and prognosis of future condition.

This data however can be massive, complex and difficult to analyze and therefore not particularly meaningful, especially to unsophisticated tester users. It has been found that a weighted assemblage of various of the data provides a simple, meaningful and quite accurate measure of at least present fruit condition, past fruit history and potential future development. This measure of fruit nature is denominated as the quality factor and represented numerically based on a numerical scale with the 100 point designation being fruit condition at optimal picking time and the 0 point being the lower limit of acceptability as a food product. The quality factor values may range both above and below the 100 range as a function of time. A graph of the quality control factor for a group of Washington State mid-Columbian Red Chief apples over a period of 100 days is shown in FIG. 10 to illustrate the general statistical development of an apple over its useful life span.

To determine the quality factor, data obtained in one or more tests are classified in several specific areas such as elastic modulus, pressure maxima and pressure averages for the R-1, R-2, R-3 zones, creep analysis, crispness analysis and starch and water core estimation. Each of these factors is given a numerical value based on the scale of 0 to 100, with the 100 value representing an optimal fruit at picking the 0 value representing the lower limit of consumer acceptability. The values so obtained then are determined for specific fruit types and a weighted average of all factors determined to provide the quality factor. This provides a quality factor numerical value which fairly accurately quantifies the growth history and condition of a particular fruit to provide a quite accurate indication of its state of maturity, its present acceptability for economic purposes and a prediction of its additional acceptable life period. The quality factor values vary with species of fruit and to some degree with growing conditions, geographic growing areas and fruit history, all of which may be determined and profiled for individual fruit species and other relevant components according to methods herein described.

The quality factor determination is a valuable tool in determining and comparing general fruit quality especially for unsophisticated users, but it does not render the determination of its individual constituents any less valuable. The individual constituents and their relationships still serve their purposes for more sophisticated analysis.

The elastic modulus of a fruit is a measure of the structural integrity of the fruit. Immediately after contacting the surface of a fruit and before any fracture, significant deformation or actual penetration of the fruit has occurred, the force loading of the plunger increases at an approximately linear rate. The slope of this loading rate curve is determined by least squares lineal regression by the computer software to arrive at what is herein termed the elastic modulus of the fruit. This elastic modulus indicates largely the structural integrity of a fruit in the R-1 zone and statistically is somewhat comparable and functionally related to the average results obtained by present day regulatory intrusive type manual testers and by various non-destructive surface impingement testers. The elastic modulus provides data for some comparison of the measures obtained by different testers to show their relationship.

The pressure maxima and averages within the three distinguished fruit zones R-1, R-2 and R-3 are determined from constant velocity pressure test measurements by ordinary known statistical methods. The maximum pressure determined in the R-1 zone will correspond somewhat to the pressure value given by the current industry standard manual pressure testers. This allows the instant tester data to be meaningfully compared to fruit maturity testing methods currently used in the agricultural industry and by regulators. The average pressure measures in the R-2 zone where the bulk of the edible fruit material resides show an empirical relationship to starch value for apples and may be used for comparison with chemically determined starch values, though functional relationships vary in various fruit species. The average and maximum pressures in the R-3 core region of an apple serve as early measures indicating the maturation process and also tend to indicate structural abnormalities such as water core, spoilage or the like where these abnormalities are likely to occur.

Creep values are a measure of the viscoelastic properties of a fruit, are functionally related to crispness, and in the R-1 and R-2 zones are empirically related to average fruit pressure. Excessive creep rates tend to indicate that a fruit is nearing undesirable maturity. Fresher fruits have lower creep values even in higher pressure fruits and increasingly high creep values occur for increasingly low pressure fruit, so the creep value serves as a sensitive measure of structural integrity and crispness of the edible portion of relatively low pressure fruit in zones R-1 and R-2. The creep in the R-2 zones of a group of good fresh and old mature Fugi apples are compared in FIG. 9. The creep displacement in the R-3 zone serves as a sensitive measure of the state of the maturation process or abnormalities that cause variation in the structural properties of a fruit.

Crispness analysis determines firmness, brittleness and crunchability of the fruit meat, generally primarily in zone R-2. A portion of the high frequency force data in zone R-2 is gathered during the constant rate testing, at a rate of about 5000 samples per second. The software then computes an equivalent reduced sample rate of 500 samples per second to compile a finite Fourier transform from a portion of this downloaded sample data. The real portion of the computed discrete Fourier transforms sequence then is raised to the second power to represent a modified spectral density power sequence and terms of this sequence are added together into frequency power buckets which are averaged to numerically determine the crispness value. The bucket values may be otherwise determined in various known fashions such as by using averages, normalization or the like. The crispness value so determined provides a numerical estimate of the desirability of fruit for consumption and is empirically related to the fruit pressure, particularly to its maximum value. Crispness analysis also serves as a secondary measure that confirms the structural quality of a fruit. It is most significant at high fruit pressure, so it is a measure that is sensitive to structural changes in higher pressure apples. Crispness also is empirically related to water core levels in fruit with higher pressure values.

Other methods of analysis of the sampling data are available and various of them are known, but the tests set forth appear at present to be the most significant in determining fruit quality, maturation and future development.

The foregoing description of our tester, the methods its use and analysis of its data are necessarily of a detailed nature so that specific embodiments of the best known modes of our invention might be set forth as required, but it is to be understood that various modifications of detail, rearrangements and multiplication of parts and modifications of ordering might be resorted to without departing from the spirit, essence or scope of the invention.

Having thusly described our invention, what we desire to protect by letters patent and

What we claim is:

1. A method for determining the maturation state and condition of a fruit with a computer serviced intrusion type plunger tester, comprising the steps of:

classifying a soft tissue fruit into three concentric zones consisting of a first zone extending spacedly inward from the fruit periphery, a third zone including the fruit core and a second zone bounded by the first and third zones;

mechanically moving an elongate plunger into the fruit through at least one data point in each of the said three zones of the fruit and determining plunger position relative to the fruit surface at each of the data points;

determining data relating to the viscoelastic properties of the fruit at each data point within the fruit;

analyzing the data relating to the viscoelestic maturation state to determine the condition and maturation state of the tested fruit.

2. The process of claim 1 further including the step of:

moving the plunger into the fruit at a constant predetermined velocity at at least one data point in each zone and measuring the pressure resisting plunger penetration into the fruit at the at least one data point in each zone.

3. The process of claim 1 wherein the data relating to the viscoelastic properties of the fruit is determined by:

maintaining the plunger in the fruit at a predetermined constant pressure at at least one data point in each zone and measuring plunger motion over a predetermined period of time at the at least one data point in each zone.

4. The process of claim 1 wherein the data relating to the viscoelastic properties of the fruit is determined by:

sequentially moving the plunger into the fruit at predetermined constant velocity and maintaining the plunger in the fruit under predetermined constant pressure for a predetermined period of time at at least one data point in each zone; and determining both force resisting plunger penetration and distance of plunger motion under constant pressure at the at least one data point in each zone.

5. The method of claim 1 further including the steps of:

classifying an apple into three concentric zones comprising an R-1 zone extending from the fruit peripheral surface radially inwardly to a depth of substantially 0.320 inch, an R-2 zone extending radially inwardly from the R-1 zone to an R-3 zone and R-3 zone comprising the core area;

determining plunger position and pressure resisting plunger penetration into the fruit at at least one data point in at least two of the three concentric zones.

6. The method of claim 1 further including the steps of:

classifying an apple into three concentric zones comprising an R-1 zone extending from the fruit peripheral surface radially inwardly to a depth of substantially 0.320 inch, an R-2 zone extending radially inwardly from the R-1 zone to an R-3 zone and an R-3 zone comprising the core area;

determining initial plunger position, moving the plunger therefrom at a predetermined constant velocity and measuring pressure resisting plunger motion at at least one data point in at least two of the three concentric zones.

7. The method of claim 1 further including the steps of:

classifying an apple into three concentric zones comprising an R-1 zone extending from the fruit peripheral surface radially inwardly to a depth of substantially 0.320 inch, an R-2 zone extending radially inwardly from the R-1 zone to an R-3 zone and an R-3 zone comprising the core area;

determining plunger position and sequentially moving the plunger into the fruit at a predetermined constant velocity to determine pressure resisting plunger penetration and maintaining the plunger in the fruit under predetermined constant pressure for at least one predetermined period of time to determine plunger penetration under constant pressure both at at least one data point in at least two of the three concentric zones.

8. The method of claim 1 further including the step of:

determining a quality factor comprising a numerical value representing fruit condition by combining numerical values of pressure resisting plunger penetration at a predetermined constant plunger velocity and plunger penetration over a predetermined time at a constant plunger pressure as determined in at least two concentric zones of the fruit.

9. The method of claim 8 further including the step of:

determining the quality factor by combining the numerical data in each of the at least two concentric zones of the fruit by averaging the numerical data from each zone, weighting the average of the data from at least one zone and combining the resultant averages for each zone.

10. The process of claim 1 further includes the step of:

measuring frequency dependent pressure resisting plunger penetration at constant plunger velocity over a predetermined sequence of data points in at least two of the three zones; and analyzing the numeric values of frequency dependent pressure variations at the sequential data points through finite Fourier transformation to derive a numeric measure representing fruit maturity and condition from the frequency dependent pressure values for comparison with similar values derived from fruit of the same type and of predetermined condition and maturation state to determine the condition and maturation state of the tested fruit.

* * * * *